United States Patent
Roe et al.

(10) Patent No.: US 6,482,191 B1
(45) Date of Patent: Nov. 19, 2002

(54) ELASTICATED TOPSHEET WITH AN ELONGATE SLIT OPENING

(75) Inventors: Donald Carroll Roe, West Chester, OH (US); Gregory Ashton, Cincinnati, OH (US); Oliver Edwin Clarke Mason, Mason, OH (US); Jörg Müller, Karben (DE); Lars Westerheide, Kelkheim (DE)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/694,751

(22) Filed: Oct. 23, 2000

(51) Int. Cl.[7] ................................................ A61F 13/15
(52) U.S. Cl. .................. 604/385.01; 604/317; 604/355; 604/385.24
(58) Field of Search ............................ 604/385.01, 317, 604/322, 327, 332, 346, 355, 356, 385.19, 385.24

(56) References Cited

U.S. PATENT DOCUMENTS

| | | | |
|---|---|---|---|
| 3,577,989 A | * | 5/1971 | Anderson |
| 4,892,536 A | | 1/1990 | DesMarais et al. ...... 604/385.2 |
| 4,990,147 A | | 2/1991 | Freeland .................. 604/385.2 |
| 5,031,248 A | * | 7/1991 | Kemper |
| 5,207,663 A | * | 5/1993 | McQueen |
| 6,132,409 A | * | 10/2000 | Vogt et al. |
| 6,168,583 B1 | * | 1/2001 | Tanji et al. |
| 6,183,458 B1 | * | 2/2001 | Ahlstrand et al. |
| 6,293,937 B2 | * | 9/2001 | Matsushita et al. |
| 2001/0023342 A1 | * | 9/2001 | Suekane |

FOREIGN PATENT DOCUMENTS

| | | |
|---|---|---|
| EP | 1106152 A1 | 6/2001 |
| GB | 2328158 A | 2/1999 |
| GB | 2329842 A | 4/1999 |
| WO | WO 98/08476 | 3/1998 |

* cited by examiner

*Primary Examiner*—Jeanette Chapman
(74) *Attorney, Agent, or Firm*—Jay A. Krebs; Jeffrey R. Moore; Eileen L. Hughett

(57) ABSTRACT

An absorbent article having a void space for receiving bodily exudates comprises an elongate slit opening in communication with the void space. The elongate slit opening includes elasticated region disposed along longitudinal side edges of the slit opening which maintain longitudinal and lateral alignment and Z-direction proximity with a point of discharge on a wearer during use. The elasticated regions contain stored elastic energy producing tensile forces which are distributed laterally away from the slit opening enabling the edges to deflect and allow bodily exudates to pass through the slit opening to the void space.

20 Claims, 4 Drawing Sheets

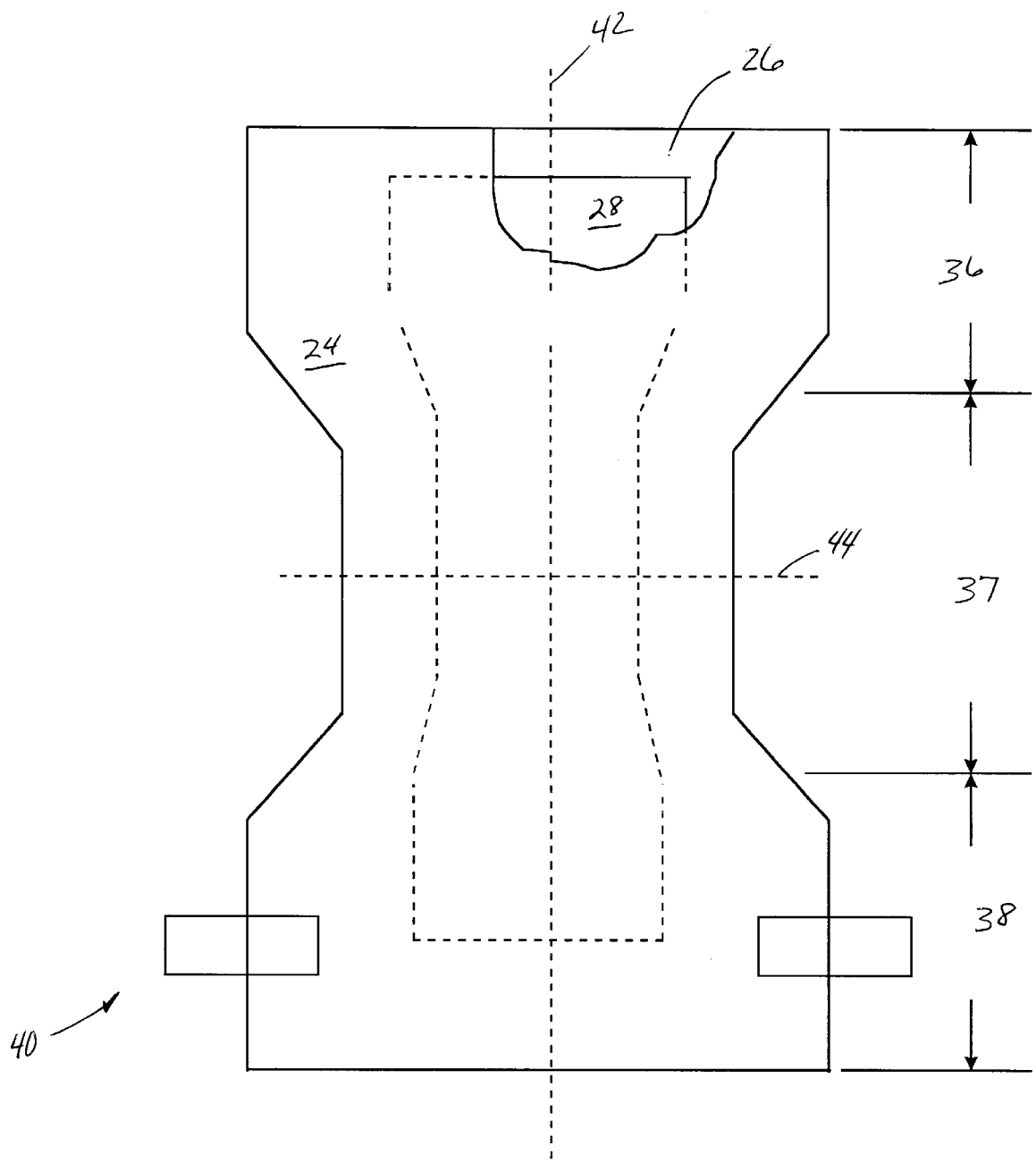
Figure: 1

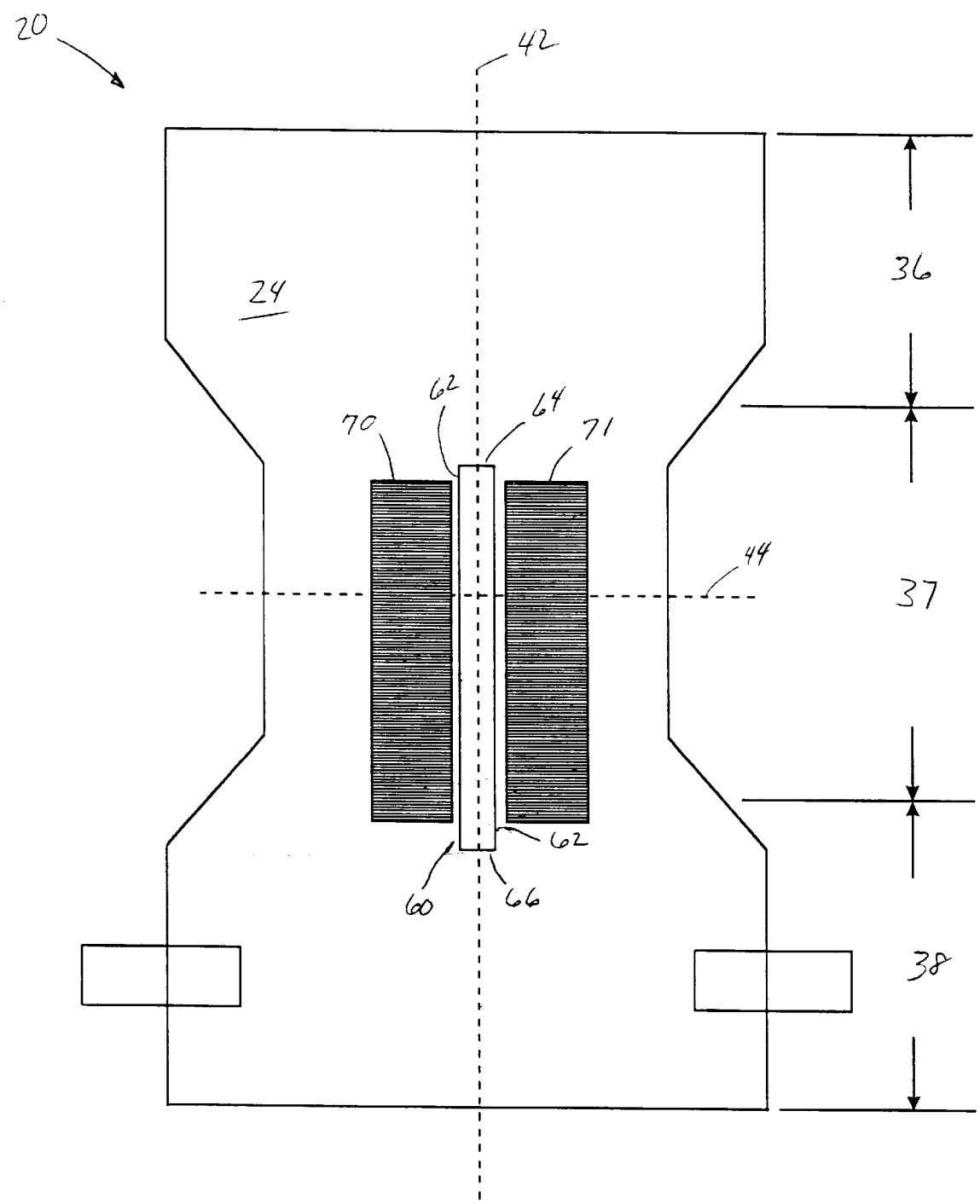
Figure: 2

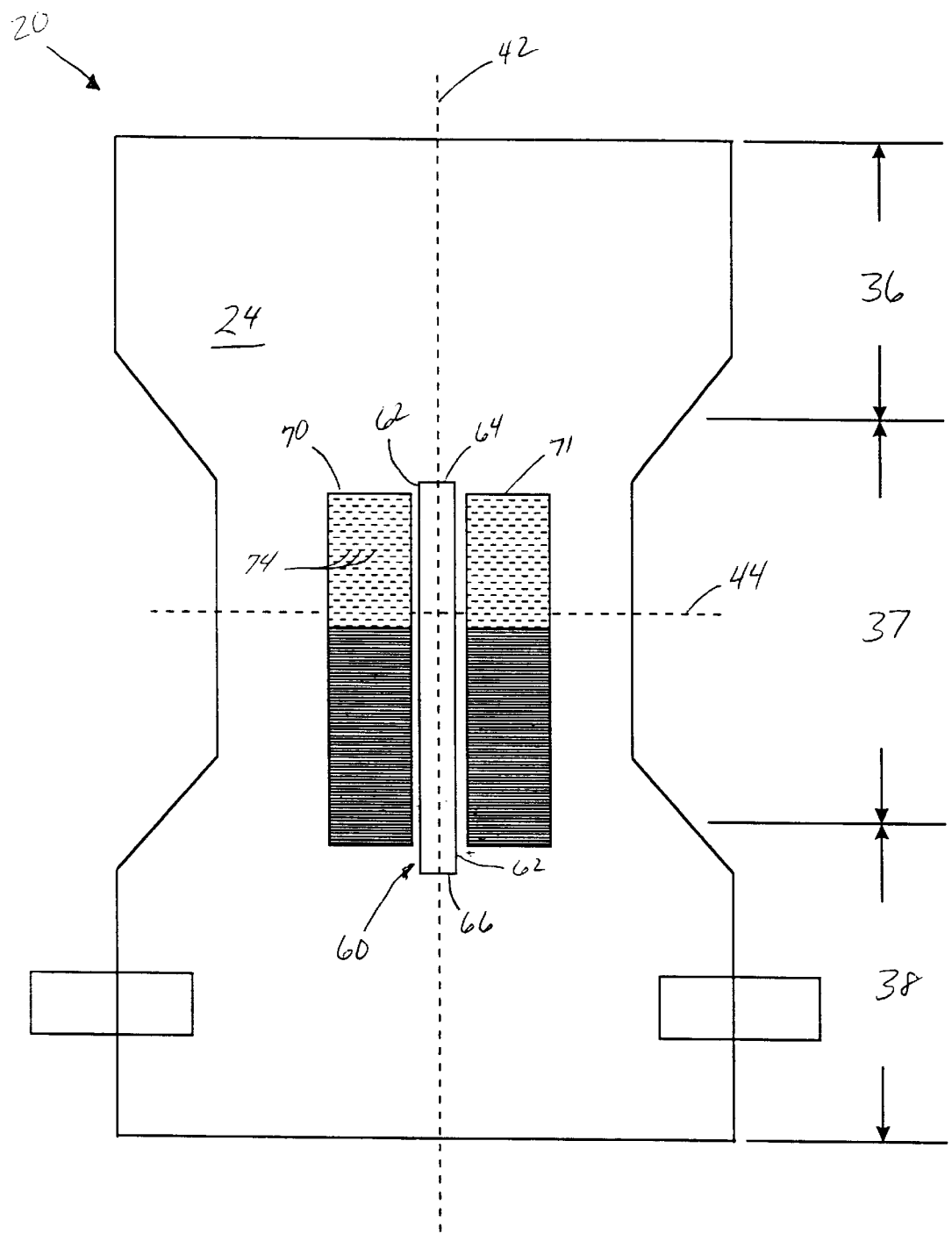
Figure: 3

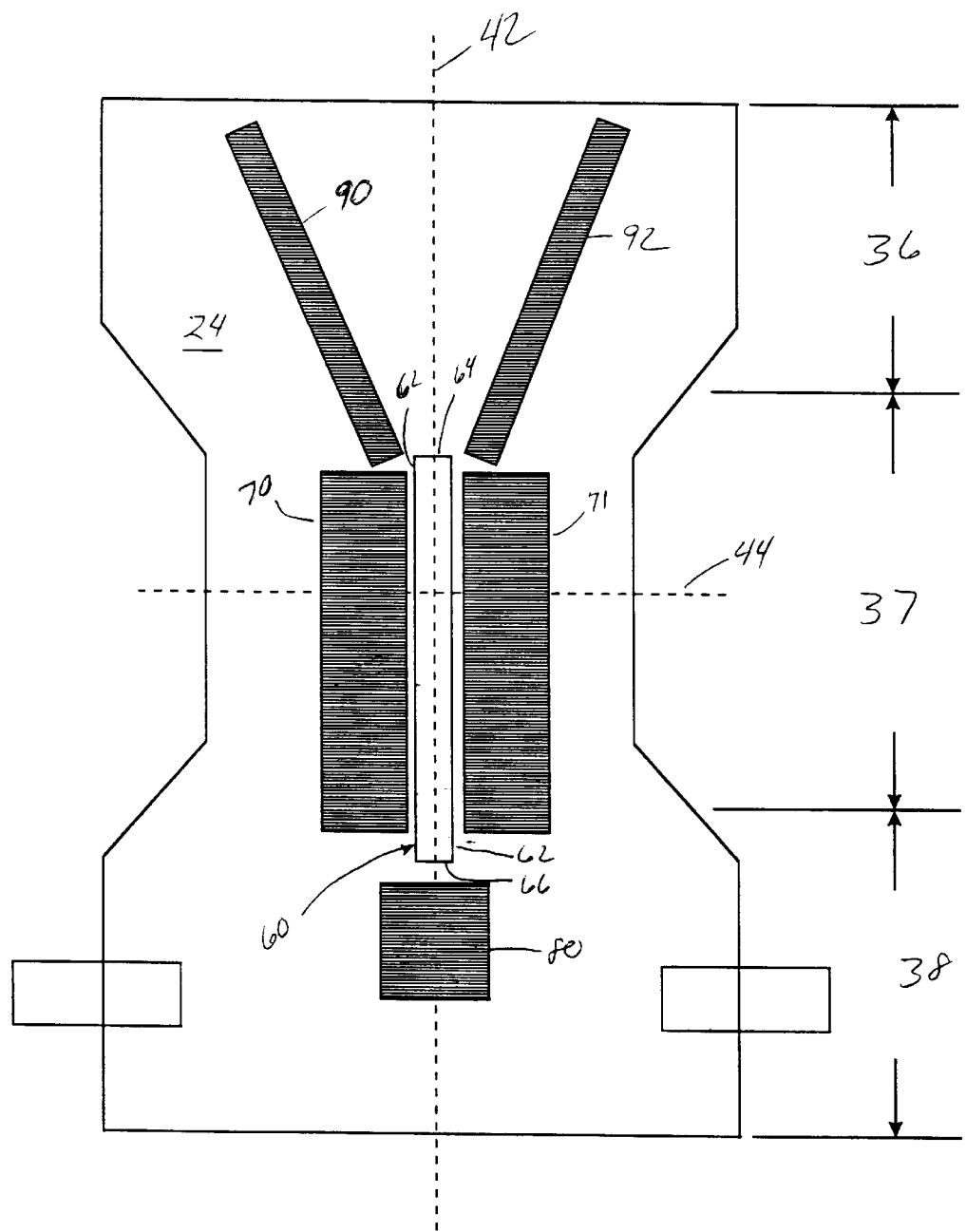
Figure: 4

ELASTICATED TOPSHEET WITH AN ELONGATE SLIT OPENING

FIELD OF THE INVENTION

This invention is directed to hygienic absorbent articles, such as diapers, training pants, adult incontinence articles, feminine protection articles and the like.

BACKGROUND OF THE INVENTION

Wearable absorbent articles are well known in the art. These articles typically have an absorbent core, which is held or positioned against the body of the wearer during use by a fastening system, such that the bodily exudates are caught by the article. Typical absorbent articles include a topsheet facing the wearer which permits fluid exudates to pass through and a backsheet which prevents the exudates from escaping from the absorbent article.

Many advancements have been made in the art since the introduction of the disposable absorbent article. However, problems still exist relating to the acceptance and storage of feces. The problem has been difficult to resolve because feces generally will not pass through a topsheet and thus, remains free to move about in the diaper until the diaper is changed. This often leads to feces escaping the diaper or soiling of the wearer's skin.

In order to prevent the feces from escaping the absorbent article or soiling the skin, apertures have been provided in the topsheet which allow the feces to pass to a void space disposed between the topsheet and underlying layers of the diaper. However, the apertures are difficult to position during application of the article and often move from the desired position when the article is worn.

Some degree of success has been achieved using an elastically foreshortened topsheet having a generally elliptical aperture to allow feces passage and retention away from the skin. These articles are disclosed in U.S. pat. No. 4,892,536 issued to DesMarais and U.S. pat. No. 4,990,147 issued to Freeland both of which are incorporated herein by reference. These approaches have the limitation of not maintaining alignment of the opening with the wearer's anus in one or more of the longitudinal, lateral or z-direction axes of the article. Further, if the opening shifts laterally to a significant degree, the opening may achieve a geometric lock on the edge of the buttocks, decreasing the likelihood of proper aperture alignment with the anus.

Thus, it would be desirable to provide an absorbent article having an aperture providing a passageway to a void space for receiving bodily exudates with improved fit and alignment capability which can be sustained during use.

SUMMARY OF THE INVENTION

In order to solve one or more of the problems found in the art, an absorbent article, such as an adult incontinence article, baby diaper, training pant or feminine hygiene pad, includes an elongate slit opening providing a passageway between a point of discharge on the wearer and a void space for receiving and storing bodily exudates. The elongate slit opening includes longitudinal elasticated side edges to maintain the opening in alignment and proximity with the point of discharge on the wearer during use.

Preferably, the absorbent article comprises a topsheet including an elongate slit opening in communication with a void space for receiving fecal waste therein, a backsheet joined with at least a portion of the topsheet, and an absorbent core disposed between at least a portion of the topsheet and the backsheet. The topsheet is foreshortened along portions of longitudinal side edges of the elongate slit opening to produce elasticated regions which contain stored elastic energy producing tensile forces which are distributed laterally away from the slit opening. The elasticated regions force the slit opening into the gluteal groove during wear, maintaining the lateral and longitudinal alignment and Z-direction proximity of the slit opening to the wearer's anus initially and throughout the wear cycle. Distributing the tensile forces laterally about the opening minimizes the concentration of stored elastic energy along the edges enabling insults of fecal matter to deflect the side edges allowing it to pass through the opening to the void space.

BRIEF DESCRIPTION OF THE DRAWINGS

While the specification concludes with claims particularly pointing out and distinctly claiming the subject matter which is regarded as forming the present invention, it is believed that the invention will be better understood from the following description which is taken in conjunction with the accompanying drawings in which like designations are used to designate substantially identical elements, and in which:

FIG. 1 is a plan view of a disposable diaper.

FIG. 2 is a plan view of a disposable diaper configuration of the present invention.

FIG. 3 is plan view of an alternate embodiment of the disposable diaper configuration shown in FIG. 2.

FIG. 4 is plan view of an alternate embodiment of the disposable diaper configuration shown in FIG. 2.

DETAILED DESCRIPTION OF THE INVENTION

While this specification concludes with claims particularly pointing out and distinctly claiming that which is regarded as the invention, it is anticipated that the invention can be more readily understood through reading the following detailed description of the invention and study of the included drawings.

The present invention provides an absorbent article having a topsheet with an elongate slit opening therein which is in communication with a void space for receiving bodily exudates. The slit opening is defined by longitudinally extending side edges having elasticated regions disposed along at least portions of the side edges. The elasticated regions maintain longitudinal and lateral alignment as well as Z-direction proximity with a point of discharge on a wearer. When the article is worn by a wearer, the elasticated regions contain stored elastic energy producing tensile forces which are distributed laterally away from the slit opening enabling bodily exudates to pass through with minimal resistance. The elongate slit opening having elasticated longitudinally extending side edges described herein is equally applicable to absorbent articles such as training pants, pant-type diapers, incontinence briefs, incontinence undergarments, absorbent inserts, diaper holders and liners, feminine hygiene garments, bandages and the like, however, a preferred embodiment of an absorbent article of the present invention is a unitary disposable absorbent article, such as the disposable diaper 20, shown in FIG. 1.

DEFINITIONS

As used herein, the following terms have the following meanings:

"Absorbent article" refers to devices which absorb and contain liquid, and more specifically, refers to devices which are placed against or in proximity to the body of the wearer to absorb and contain the various exudates discharged from the body.

"Longitudinal" is a direction running parallel to the maximum linear dimension of the article and includes directions within ±45° of the longitudinal direction.

The "lateral" or "transverse" direction is orthogonal to the longitudinal direction.

The "Z-direction" is orthogonal to both the longitudinal and transverse directions.

The term "disposable" is used herein to describe absorbent articles which generally are not intended to be laundered or otherwise restored or reused as an absorbent article (i.e., they are intended to be discarded after a single use and, preferably, to be recycled, composted or otherwise disposed of in an environmentally compatible manner).

As used herein, the term "disposed" is used to mean that an element(s) is formed (joined and positioned) in a particular place or position as a unitary structure with other elements or as a separate element joined to another element.

As used herein, the term "joined" encompasses configurations whereby an element is directly secured to another element by affixing the element directly to the other element, and configurations whereby an element is indirectly secured to another element by affixing the element to intermediate member(s) which in turn are affixed to the other element.

A "unitary" absorbent article refers to absorbent articles which are formed of separate parts united together to form a coordinated entity so that they do not require separate manipulative parts like a separate holder and liner.

As used herein, the term "diaper" refers to an absorbent article generally worn by infants and incontinent persons about the lower torso.

As used herein, the term "void space" is a cavity sized to accept bodily exudates such as fecal material.

FIG. 1 is a plan view of the diaper 20 in its flat out, uncontracted state (i.e., without elastic induced contraction) with portions of the structure being cut away to more clearly show the underlying structure of the diaper 20 and with the portion of the diaper 20 which contacts the wearer facing the viewer. One end portion of the diaper 20 is configured as a first waist region 36 of the diaper 20. The opposite end portion is configured as a second waist region 38 of the diaper 20. An intermediate portion of the diaper 20 is configured as a crotch region 37 which extends longitudinally between the first and second waist regions 36 and 38. The waist regions 36 and 38 generally comprise those portions of the diaper 20 which, when worn, encircle the waist of the wearer. The waist regions 36 and 38 may include elastic elements such that they gather about the waist of the wearer to provide improved fit and containment. The crotch region 37 is that portion of the diaper 20 which, when the diaper 20 is worn, is generally positioned between the legs of the wearer.

The diaper 20 preferably comprises a liquid previous topsheet 24, a liquid impervious backsheet 26, and an absorbent core 28 encased between the topsheet 24 and the backsheet 26. The topsheet may include regions of reduced permeability to fecal material. The topsheet 24 may be fully or partially elasticated or may be foreshortened so as to provide a void space between the topsheet 24 and the core 28. Exemplary structures including elasticized or foreshortened topsheets are described in more detail in U.S. Pat. No. 4,892,536 issued to DesMarais et al. on Jan. 9, 1990 entitled "Absorbent Article Having Elastic Strands"; U.S. Pat. No. 4,990,147 issued to Freeland on Feb. 5, 1991 entitled "Absorbent Article With Elastic Liner For Waste Material Isolation"; U.S. Pat. No. 5,037,416 issued to Allen et al. on Aug. 6, 1991 entitled "Disposable Absorbent Article Having Elastically Extensible Topsheet"; and U.S. Pat. No. 5,269,775 issued to Freeland et al. on Dec. 14, 1993 entitled "Trisection Topsheets For Disposable Absorbent Articles and Disposable Absorbent Articles Having Such Trisection Topsheets"; each of which is incorporated by reference herein.

The diaper 20 preferably also includes a fastener such as a hook and loop type fastening system 40 including at least one engaging component (male fastening component) and at least one landing zone (female fastening component). The diaper 20 may also include such other features as are known in the art including leg cuffs, front and rear ear panels, waist cap features, elastics and the like to provide better fit, containment and aesthetic characteristics. Such additional features are well known in the art and are described in U.S. Pat. No. 3,860,003; and U.S. Pat. No. 5,151,092 which are incorporated by reference herein.

In addition, the present invention may be suitable for other diaper embodiments including those disclosed in U.S. Pat. No. 6,010,491 titled "Viscous Fluid Bodily Waste Management Article" issued Jan. 4, 2000; U.S. Pat. No. 5,873,870 titled "Fit And Sustained Fit Of A Diaper Via Chassis And Core Modifications" issued Feb. 23, 1999; U.S. Pat. No. 5,897,545 titled "Elastomeric Side Panel for Use with Convertible Absorbent Articles" issued Apr. 27, 1999; U.S. Pat. No. 5,904,673 titled "Absorbent Article With Structural Elastic-Like Film Web Waist Belt" issued May 18, 1999; U.S. Pat. No. 5,931,827 titled "Disposable Pull On Pant" issued Aug. 3, 1999; U.S. Pat. No. 5,977,430 titled "Absorbent Article With Macro-Particulate Storage Structure" issued Nov. 2, 1999 and U.S. Pat. No. 6,004,306 titled "Absorbent Article With Multi-Directional Extensible Side Panels" issued Dec. 21, 1999, the disclosures of which are incorporated herein by reference.

The present invention is particularly suited to the entrapment or encapsulation of bodily waste in order to reduce the amount and area of contamination of the wearer's skin by the waste. In addition to elongate slit openings having elasticated longitudinally extending side edges providing a passageway to a void space, other embodiments of the present invention for limiting the movement of waste and/or providing the containment thereof may include pockets for receiving and containing waste, barriers for limiting the movement of waste in the article, compartments or voids which accept and contain waste materials deposited in the diaper 20, and the like, or any combinations thereof. Examples of pockets and spacers for use in absorbent products are described in U.S. Pat. No. 5,514,121 issued to Roe et al. on May 7, 1996, entitled "Diaper Having Expulsive Spacer"; U.S. Pat. No. 5,171,236 issued to Dreier et al. on Dec. 15, 1992 entitled "Disposable Absorbent Article Having Core Spacers"; U.S. Pat. No. 5,397,318 issued to Dreier on Mar. 14, 1995 entitled "Absorbent Article Having A Pocket Cuff"; U.S. Pat. No. 5,540,671 issued to Dreier on Jul. 30, 1996 entitled "Absorbent Article Having A Pocket Cuff With An Apex"; PCT Application WO 93/25172 published Dec. 3, 1993 entitled "Spacers For Use In Hygienic Absorbent Articles And Disposable Absorbent Articles Having Such Spacer"; U.S. Pat. No. 5,306,266 entitled "Flexible Spacers For Use In Disposable Absorbent Articles" issued to Freeland on Apr. 26, 1994; and U.S. Pat. No. 5,997,520 entitled "Disposable Absorbent Article With Selectively Expandable or Inflatable Component" issued to Ahr et al. on Dec. 7, 1999. Examples of compartments or voids are disclosed in U.S. Pat. No. 4,968,312 entitled "Disposable Fecal Compartmenting Diaper" issued to Khan on Nov. 6, 1990; U.S. Pat. No. 4,990,147 entitled "Absorbent Article With Elastic Liner For Waste Material Isolation" issued to Freeland on Feb. 5, 1991; U.S. Pat. No. 5,62,840, entitled "Disposable Diapers" issued to Holt et al on Nov. 5, 1991; and U.S. Pat. No. 5,269,755 entitled "Trisection Topsheets For Disposable Absorbent Articles And Disposable Absorbent Articles Having Such Trisection Topsheets" issued to Freeland et al on Dec. 14, 1993. Examples of suitable transverse barriers are described in U.S. Pat. No. 5,554,142 entitled "Absorbent Article Having Multiple Effective Height Transverse Partition" issued Sep. 10, 1996 in the name of Dreier et al.; PCT Patent WO 94/14395 entitled "Absorbent Article Having An Upstanding Transverse Partition" published Jul. 7, 1994 in the name of Freeland, et al.; and U.S. Pat. No. 5,653,703 Absorbent Article Having Angular Upstanding Transverse Partition issued Aug. 5, 1997 to Roe, et al. Examples of other structures especially suitable for management of low viscosity feces are disclosed in U.S. Pat. No. 5,941,864 issued to Roe et al. on Aug. 24, 1999; U.S. Pat. No. 5,977,430 issued to Roe et al. on Nov. 2, 1999 and U.S. Pat. No. 6,013,063 issued to Roe et al. on Jan. 11, 2000. All of the above-cited references are hereby incorporated by reference herein.

In order to achieve the desired level of entrapment or encapsulation of bodily waste, especially for viscous bodily waste such as feces, at least two functions should be performed. First, the diaper should provide a passageway from a wearer's anus through a topsheet to a void space in the diaper which can be initially aligned with the anus when the diaper is fitted to the wearer and maintained throughout the wear cycle. Second, the passageway should enable bodily waste to freely pass through to the void space with minimal resistance.

The topsheet 24 of the diaper 20 of the present invention is shown in FIG. 2. The topsheet 24 includes a slit opening 60 therein which is configured to receive fecal exudates and isolate at least a portion of the exudates from the skin of the wearer. The slit opening 60 is located in the topsheet 24 such that the fecal exudates pass through the opening into a void space formed between the topsheet 24 and the absorbent core 28 and/or other underlying layers such as sub layers, acquisition layers and the like. The void space entraps or encapsulates bodily waste. It is also contemplated that the void space may be formed between two elements of the diaper 20, including but not limited to the topsheet 24 and the backsheet 26, the acquisition layer and the core 28, the core 28 and the backsheet 26, etc. Alternatively, the void space may be formed between a secondary topsheet and a primary topsheet which are disposed in a face-to-face arrangement and joined along the edges such that the secondary topsheet faces the skin of the wearer and the primary topsheet faces the underlying layers. For this embodiment, the void space is in communication with a slit opening in the secondary topsheet.

The slit opening 60 in the topsheet 24 is located in alignment with the wearer's anus during use. Preferably, the slit opening 60 in the topsheet 24 is located in a target zone of the diaper. The target zone is that portion of the diaper which is configured to directly receive the insult of fecal matter from the wearer and is generally located in the crotch portion of the diaper. Particularly, in one non-limiting embodiment, the target zone may extend from about 5 to about 20 centimeters in length along the longitudinal axis 42 of the diaper with about one fourth of its length extending longitudinally from the lateral axis 44 of the diaper 20 towards the first waist region 36 and the remainder extending longitudinally towards the second waist region 38, when measurements are made with the topsheet in a fully extended state. Generally, about 0% to about 40% of the slit opening 60 may be located forward of the lateral centerline 44 on the diaper 20.

The slit opening 60 in the topsheet 24 is generally disposed in the target zone along the longitudinal axis 42 and is defined by two opposing longitudinally extending side edges 62, a front edge 64 and a back edge 66. The front edge 64 is generally located in the crotch region 37 of the diaper 20 towards the first waist region 36 while the back edge 66 is located in the crotch region 37 near the second waist region 38. The slit opening 60 includes a length in the longitudinal direction parallel to the longitudinal axis 42 of the diaper and a width in the lateral direction which is parallel to the lateral axis 44 of the diaper 20. The length of the slit opening 60 ranges from about 5 cm to about 20 cm, preferably from about 12 cm to about 18 cm, while the width ranges from about 0 cm to about 2 cm, preferably between about 0.2 cm and 0.5 cm. The aspect ratio of the slit opening which is the ratio of the longitudinal length to the lateral width generally ranges from about 5 to about 100, and preferably at least about 15.

The advantages of a diaper including an opening in the topsheet 24 in communication with a void space are significantly reduced if the opening in the topsheet does not stay aligned with the point of discharge (i.e. wearer's anus) throughout the time of use (or at least until the wearer has a bowel movement). Accordingly, the diaper 20 of the present invention includes an elastically foreshortened topsheet including elasticated regions 70, 71 along at least portions of the longitudinal edges 62 of the slit opening 60 which store elastic energy and induce tensile loading along the edges 62 when fitted to the wearer. This stored elastic energy/tensile loading causes the slit opening 60 to settle in the area of least resistance (i.e., position in which the elastic is most relaxed). For a fitted diaper or training pant, the area of least resistance is the gluteal groove of the buttocks, including the perianal region. When the diaper 20 is fitted to the wearer, the tensile loading locates the slit opening 60 against the skin near the wearer's anus and maintains longitudinal and lateral alignment as well as the Z-direction proximity to the anus during the wear cycle, in order to facilitate preferential passage of feces through the slit opening 60 versus the region between the topsheet 24 and the wearer's skin.

The longitudinal extension of the topsheet 24 in use may vary based on the body dimensions of the individual wearer, different application habits by the caregiver, or even a shift of the product on the wearer during the wear cycle, such as sagging of the diaper. The elastically foreshortened topsheet preferably maintains the elastic forces in the desired range for all typical in-use topsheet extensions. In certain preferred embodiments of the present invention, in-use topsheet lengths for diapers designed for size 4 babies may be in the range of 25 to 35 cm. The desired in use return forces induced by the elasticated regions 70, 71 of topsheets at these extended lengths are in the range from about 0.05 N to about 5 N and in the range of about 0.2 N to about 1 N with an in use return force of about 0.5 N being most desirable. The corresponding in use force distributions of the elasticated regions 70, 71 in terms of force per unit lateral dimension can range from about 0.01 N/cm to about 3 N/cm and from about 0.05 N/cm to about 1.0 N/cm with anise force distribution range of about 0.1 N/cm to about 0.5 N/cm being most desirable. Higher forces may result in unwanted skin irritation or pressure marking where as lower forces may not provide the desired functionality.

In addition to maintaining alignment with the wearer's anus, the tensile forces induced by elasticated regions along the longitudinal edges 62 of the slit opening 60 must allow fecal matter to pass through the slit opening 60. As the elasticated longitudinal edges 62 force the slit opening 60 into the gluteal groove of the wearer, the longitudinal edges 62 are forced together, effectively closing off the opening from the void space. Accordingly, the stored elastic energy along the edges of the slit opening is preferably minimized to enable fecal matter to deflect the edges 62 and pass through the slit opening 60 into the void space during normal bowel movements, while maintaining the previously mentioned longitudinal, lateral and Z-direction alignment performance (i.e., coordination of the slit opening with the anus). Accordingly, for optimal BM isolation performance of the topsheet 24, it is desirable that the total stored elastic energy in the regions laterally outboard of the slit opening 60 be sufficiently high to facilitate the alignment of the slit opening 60 with the anus and the penetration of the slit edges 62 into the gluteal groove, while maintaining a sufficiently low stored elastic energy in the region of the topsheet 24 immediately adjacent the slit edge 62 to allow penetration of the slit opening 60 by feces during defecation. This may be accomplished by distributing the stored elastic energy laterally outboard of the slit opening 60. Alternatively, the edges 62 of the slit opening may be held against the skin, allowing the feces to penetrate the slit opening 60 without deflection, via a body adhering composition as described herein or sufficient stored elastic energy.

The elasticated regions 70, 71 may be formed by foreshortening the topsheet by bonding prestretched elastic members storing elastic energy along at least portions of the longitudinal edges 62 of the slit opening 60 which can induce tensile forces that are substantially aligned with the longitudinal axis 42 of the topsheet. For this embodiment, the elasticated regions 70, 71 cover areas along the longitudinal side edges 62 distributing the stored elastic energy laterally away from the longitudinal edges 62 of the slit opening 60 in order to minimize the tensile forces concentrated along the slit edges 62.

The width of the elasticated regions 70, 71 measured laterally from the longitudinal edges 62 of the slit opening ranges from about 5 mm to about 50 mm, and generally at least about 10 mm. The elasticated regions 70, 71 laterally outboard of the slit opening 60 may have a steady-state stored elastic energy distribution in the lateral direction of no more than about 20 mJ per mm of width, preferably no more than about 10 mJ/mm, and most preferably no more than about 5 mJ/mm, when the elasticated region 70, 71 or member, is stretched to a length about 67% greater than its relaxed length or to its full extension, whichever occurs first. More preferably, the elasticated regions 70, 71 laterally outboard of the slit opening 60 may have a steady-state stored elastic energy distribution in the lateral direction of no more than about 20 mJ per mm of width, preferably no more than about 10 mJ/mm, and most preferably no more than about 5 mJ/mm, when the elasticated regions, or member, is stretched to a length about 100% greater than its relaxed length or to its full extension, whichever occurs first. Generally the stored elastic energy distribution ranges from about 1 mJ/mm to about 25 mJ/mm, and preferably from about 2 mJ/mm to about 10 mJ/mm when the elasticated member is extended to a length at least about 67% greater than its relaxed length. Additionally, the total steady-state stored elastic energy along the edges 62 of the slit opening 60 is at least about 50 milli Joules (mJ), and generally in the range of about 100 mJ to about 500 mJ, when the topsheet is in its fully extended state. For example, a topsheet for a Size 4 Pampers Premium diaper, available from the Procter and Gamble Co. Cincinnati, Ohio, designed for a wearer's weight range of 21 lb to 37 lb, may have a length of about 501.7 millimeters in its fully extended state. In general, the total steady-state stored energy in the elastic region along the slit edges may range from about 50 mJ to about 1000 ml when the topsheet is fully extended.

The topsheet 24 preferably also has a stored steady-state energy when extended from its relaxed state to a length less than its fully extended length. For example, the topsheet may have a stored energy of at least about 50 ml when extended to 67% of its fully extended length. The topsheet preferably has a relaxed length smaller than the "rise" of the wearer (i.e., the distance from the navel to the small of the back as measured through the wearer's crotch) to ensure that energy is stored in the topsheet by the caregiver during the application of the product. Preferably, the relaxed length of the topsheet is less than about 80% of the fully extended length of the topsheet. More preferably, the relaxed length of the topsheet is less than about 60% of the fully extended length of the topsheet. Most preferably, the relaxed length of the topsheet is less than about 50% of the fully extended length of the topsheet.

In a non-limiting example referred to hereinafter as Example 1, an elastic film available as VFE X25007, available from Tredegar Corporation of Terre Haute, Ind., is applied in a stretched condition to a polypropylene nonwoven, available as P-14 from Veratec, Inc. of Walpole, Mass. The nonwoven film is 50 mm wide and 76 mm long (i.e., in the direction of stretch) in a relaxed state. A 6 mm region of the elastic film should be deadened at each end of the piece of film. The elastic film is then stretched to a length of 240 mm and affixed to the underside of the nonwoven centered along the longitudinal axis of the nonwoven to form the elasticated topsheet. The rear edge of the elastic film is located 64 mm from the rear edge of the nonwoven (i.e., the edge intended to be in the rear waist region of a finished diaper. A 160 mm long by 5 mm wide slit is made along the longitudinal axis of the elastic film/nonwoven laminate (the total width of the elasticated region associated with the regions laterally outboard of the slit region is 45 mm due to the removal of 5 mm of the elastic film). The rearward end of the slit is located 68 mm from the rear end of the elastic film. The relaxed length of the slit is 55 mm. The relaxed length of the topsheet is 245 mm. The topsheet may be used on a Pampers Premium Size 4 diaper, designed for a baby weight range of 21–37 pounds. This topsheet is referred to hereinafter as Example 1.

In a comparative example referred to hereinafter as comparative example 1, a topsheet is made using Lycra strands, available as 940 Desitex Lycra from DuPont de Nemours, E. I. & Co., Inc. of Wilmington, Del. The Lycra strands have a width of 0.5 mm. Two Lycra strands, each having a relaxed length of 65 mm are stretched to a length of 225 mm and affixed adjacent to each other to the underside of a P-14 nonwoven. A 160 mm slit is cut in the nonwoven between the Lycra strands. The relaxed length of the slit is about 53 mm. The topsheet has a relaxed length of 225 mm. This topsheet is referred to hereinafter as Comparative Example 1. Data on Comparative Example 1 and Example 1 are provided in Table 1 below:

TABLE 1

| | Comparative Example 1 | Example 1 |
|---|---|---|
| Steady-state stored energy (mJ) @ 100% extension | 78 | 460 mJ |
| Steady-state stored energy (mJ) @ 67% extension | 36 mJ | 250 mJ |
| Steady-state energy lateral distribution (mJ/mm) | | |
| @ 100% extension | 78 | 5.6 |
| @ 67% extension | 36 | 10.3 |
| Relaxed length to extended length ratio | .46 | .49 |
| Pass-through work required (mJ) @ 100% extension | 34 | 24 |

The dimensions and other parameters of the exemplary diaper embodiment (Example 1) described above can be readily modified by one skilled in the art to smaller or larger wearers, including adult wearers.

In certain preferred embodiments of the present invention the elastic modulus of the elasticized regions 70, 71 along the longitudinal edges 62 of the elongated slit opening 60 may vary either in the lateral or longitudinal directions. For example, the elastic modulus may be higher toward the back end 66 of the slit 60 to promote the penetration and alignment of the slit 60 with the gluteal groove and anus, but may be lower toward the front end 64 of the slit 60 in proximity to the anus itself to facilitate fecal passage through the slit 60. A variable elastic modulus may be provided in any means known in the art, including use of different materials or variable numbers of layers of a given material in different portions of the elasticized regions 70, 71, mechanically modifying the topsheet 24 associated with different portions of the elasticized regions 70, 71, or by slitting the elastic material in certain regions. For example, FIG. 3 shows a non-limiting embodiment of the invention wherein the elasticized material includes a pattern of slits 74 in the region associated with the anus to reduce the elastic modulus in this area to promote fecal passage. In certain embodiments of the present invention, the elastic modulus of the elastic regions along at least a portion of the front half of the slit opening 60 may be about 50% lower the elastic modulus of the elastic regions along at least a portion of the back half of the slit opening 60. In these embodiments, the elastic modulus in the front region of the slit opening is generally between about 10% and 60% of the elastic modulus in the back region of the slit opening 60.

In alternate embodiments shown in FIG. 4, other elasticated regions are included in the topsheet 24 to enhance and maintain the alignment of the slit opening 60 during a wear cycle. For example, the topsheet 24 may include a rear elasticated region 80 disposed near the second end 66 of the slit opening 60, aligned with the longitudinal axis 42. In addition, the topsheet 24 may include two front elasticated regions 90, 92. The front elasticated regions 90, 92 can be disposed near the first end 64 of the slit opening 60 and extend from the crotch region 37 toward the first waist region 36 at a nonzero angle from the longitudinal axis 42 such that the two front elasticated regions 90, 92 diverge away from one another from the slit opening 60 towards the first waist region 36. The back elasticated region 80 has a total steady-state stored elastic energy of at least about 50 mJ, and generally between about 50 and 200 mJ, when the topsheet 24 is in its fully extended state. The two front elasticated regions 90, 92 have a total steady-state stored elastic energy of at least about 50 mJ, and generally between about 50 and 500 mJ, when the topsheet 24 is in it fully extended state.

In one embodiment, the diaper 20 includes a topical adhesive or body adhering composition which acts to hold the slit opening in the topsheet 24 in place during use. In these embodiments, the slit edge is held against the wearers skin in proximity to the anus and may not deflect away from the skin during defecation. The topical adhesive may be located on the topsheet 24. However, the body adhering composition may also be integral with the material making up the topsheet 24 or other element of the absorbent article or may be a separate material disposed directly or indirectly on all or any portion of the absorbent article. Further, the body adhering composition may be disposed on any portion of the absorbent article in any pattern or configuration including, but not limited to lines, stripes, dots, and the like.

In one preferred embodiment, the topical adhesive 50 is disposed on the topsheet 24 in along the longitudinal edges of the elongate slit opening. However, embodiments are contemplated wherein the topical adhesive 50 surrounds only a portion of the elongate slit opening and/or is disposed in locations not directly adjacent the elongate slit opening, such as around the edge of the topsheet 24, on the leg cuffs 32 or in one or both of the waist regions.

Types of body adhering composition may include any one or more substances capable of releasably adhering to the skin of the wearer. Further, the body adhering composition may be in the form of a gel, lotion, film, web or the like. Examples of suitable body adhering compositions include adhesives, gelatin, petrolatum, waxes such as silicone or petroleum waxes, oils such as silicone or petroleum based oils, skin care compositions or ingredients thereof, as described below, and the like. Suitable topical adhesives include, but are not limited to, hydrogel or hydrocolloid adhesives such as acrylic based polymeric adhesives, and the like. (Some exemplary hydrogel and/or hydrocolloid adhesives are disclosed in U.S. Pat. Nos. 4,231,369; 4,593,053; 4,699,146; 4,738,257; and 5,726,250; each of which is incorporated by reference herein.) The topical adhesives may also include any "medical adhesive" which is compatible for use with biological tissue, such as skin. Acrylic medical adhesives suitable for use as body adhering compositions, include adhesives available from Adhesive Research, Inc., of Glen Rock, Pa., under the designations MA-46, MA-312, "MTTM" High MVTR adhesive, and AS-17. Rubber-based medical adhesives, such as SB-2 from Adhesive Research Inc. may also be suitable. Other exemplary adhesives include Dow Corning Medical Adhesive (Type B) available from Dow Corning, Midland, Mich.; "MEDICAL ADHESIVE" from Hollister Inc., of Libertyville, Ill.; 3M Spray Adhesives #79, 76, 77 and 90 available from the 3M Corp. of St. Paul, Minn.; and "MATISOL" liquid adhesive available from Ferndale Laboratories of Ferndale, Mich. Other medical adhesives are described in U.S. Pat. Nos. 4,078,568; 4,140,115; 4,192,785; 4,393,080; 4,505,976; 4,551,490; 4,768,503 and polyacrylate and polymethacrylate hydrogel adhesives are disclosed in U.S. Pat. Nos. 5,614,586 and 5,674,275; the disclosure of each of which is incorporated by reference herein. Yet another exemplary adhesive comprising polyvinyl pyrollidone and a multi-functional amine-containing polymer is disclosed in WO 94/13235A1. (The disclosure of each of these references is incorporated herein by reference.) Alternative body adhering means which may be used in place of or in addition to those described above include static electricity, suction and the like. In any case, it is preferred that the body adhering composition permit vapors to pass (i.e., breathable), be compatible with the skin and otherwise skin friendly. Further, it is preferred that the body adhesive be at least partially hydrophobic, preferably 60%, more preferably 80%, by weight of the adhesive consist of hydrophobic components. However, hydrophilic adhesives are contemplated in certain embodiments of the present invention.

Calculating Steady-state Stored Elastic Energy in an Elastic Member

The stored energy within an elastic member is generally measured with the elastic member separate from the disposable absorbent article for which it is designed or to which it was joined during manufacture. The elastic member may include the entire topsheet or a portion thereof The relaxed length of the elastic member is recorded. The elastic member is then stretched at a rate of 254 mm/minute via an Instron or similar device (i.e., a device that can measure force as a function of elongated distance for an elastic member) to a defined length (e.g., may be the fully extended length or a fraction thereof) and held for 30 seconds. The force measured in the elastic member 30 seconds after the completion of the extension of the member is recorded as the steady-state tension. The steady-state stored energy in the elastic member is calculated by measuring the area in units of gram-seconds under the stress-strain curve during the extension cycle at a point associated with the steady-state tension recorded above and is reported in millijoules. The stored steady-state energy distribution in the lateral direction is calculated by dividing the steady-state stored elastic energy, as calculated above, by the width (i.e., the lateral dimension) of the elastic member and is reported in milli Joules of energy per millimeter of elastic member width (mJ/mm).

Pass-Through Work

Pass-through work is a measure of the energy required to push a simulated fecal bolus through the slit while the slit is in an extended state (e.g., 67% extension or full extension). The topsheet is held at both ends in tension at a fixed length. A conical plastic probe having an angle of 40 degrees and a length of 40 mm is aligned with the slit and pushed through the slit via a Stevens Texture Analyzer (details in other cases) at a rate of 90 mm per minute. The force required to push the probe through the slit is measured as a function of time/distance. The Pass-through work is the area under the force versus distance curve and is reported in mJ.

While particular embodiments and/or individual features of the present invention have been illustrated and described, it would be obvious to those skilled in the art that various other changes and modifications can be made without departing from the spirit and scope of the invention. Further, it should be apparent that all combinations of such embodiments and features are possible and can result in preferred executions of the invention. Therefore, the appended claims are intended to cover all such changes and modifications that are within the scope of this invention.

What is claimed is:

1. A wearable article having a longitudinal axis, a first waist region, a second waist region, and a crotch region interposed therebetween, the wearable article comprising a topsheet, a backsheet, and an absorbent core interposed between the topsheet and the backsheet, the topsheet comprising:
an elongate slit opening providing a passageway to a primary void space for receiving bodily exudates therein; the elongate slit opening is disposed in the crotch region along the longitudinal axis having a first end oriented towards the first waist region and a second end oriented towards the second waist region; the elongate slit opening including longitudinally opposing side edges having elasticated regions disposed along at least a portion of each of the side edges to maintain longitudinal and lateral alignment and Z-direction proximity of the slit opening with a point of discharge on the wearer, the elasticated regions containing stored elastic energy producing tensile forces which are distributed laterally away from the slit opening.

2. The wearable article as defined in claim 1 wherein the elasticated regions have variable elastic moduli that increase longitudinally from a low modulus near the front end of the slit opening to a high modulus near the back end of the slit opening.

3. The wearable article as defined in claim 2 wherein the variable elastic moduli are produced by cutting a pattern of slits in the elasticated regions.

4. The wearable article as defined in claim 2 wherein the elasticated regions have variable elastic moduli that increase laterally away from the edges of the slit opening.

5. The wearable article as defined in claim 1 wherein the elasticated regions enable the edges to deflect and allow bodily exudates to pass through the slit opening.

6. The wearable article as defined in claim 1 wherein the elasticated regions maintain the Z-direction proximity of the slit opening as bodily exudates pass through the slit opening.

7. The wearable article as defined in claim 1 further comprising a rear elasticated region disposed in the second waist region near the second end of the elongate slit opening providing a tensile force substantially aligned with the longitudinal axis.

8. The wearable article as defined in claim 1 further comprising two front elasticated regions diverging from the longitudinal axis near the first end of the elongate slit opening into the first waist region.

9. The wearable article as defined in claim 1 wherein the topsheet further comprises a topical adhesive disposed around a portion of the slit opening.

10. The wearable article as defined in claim 1 wherein the elongate slit opening has a length ranging from about 5 cm to about 20 cm.

11. The wearable article as defined in claim 1 wherein the elongate slit opening is defined by an aspect ratio wherein the aspect ratio ranges from about 5 to about 100.

12. The wearable article as defined in claim 1 wherein the elasticated regions comprise a total stored elastic energy of at least about 50 milli Joules.

13. The wearable article as defined in claim 1 wherein the elasticated regions generate an in use return force in the topsheet ranging from about 0.05 N to about 5 N.

14. The wearable article as defined in claim 1 wherein the elasticated regions have a stored energy distribution of about 50 mJ/ilinear cm.

15. The wearable article as defined in claim 1 wherein the elasticated regions have an in use force distribution ranging from about 0.01 N/cm to about 3 N/cm.

16. The wearable article as defined in claim 1 wherein the elasticated regions have a width in a range of about 5 mm to about 50 mm.

17. A disposable diaper having a longitudinal axis, a first waist region, a second waist region, and a crotch region interposed therebetween, the disposable diaper comprising:
a backsheet;
a primary topsheet joined to the backsheet;
an absorbent core disposed intermediate the backsheet and the primary topsheet;

a secondary topsheet covering at least a portion of the primary topsheet and joined thereto to form a primary void space for receiving fecal matter therein, the secondary topsheet including an elongate slit opening in communication with the primary void space; the elongate slit opening is disposed in the crotch region along the longitudinal axis having a first end oriented towards the first waist region and a second end oriented towards the second waist region; the elongate slit opening including longitudinally opposing side edges having elasticated regions disposed along at least a portion of each of the the side edges to maintain longitudinal and lateral alignment and Z-direction proximity of the slit opening with a point of discharge on the wearer, the elasticated regions containing stored elastic energy producing tensile forces which are distributed laterally away from the slit opening.

18. The wearable article as defined in claim 17 wherein the elasticated regions enable the edges to deflect and allow bodily exudates to pass through the slit openings.

19. The wearable article as defined in claim 17 wherein the elasticated regions maintain the Z-direction proximity of the slit opening as bodily exudates pass through the slit opening.

20. The disposable diaper as defined in claim 9 further comprising a rear elasticated region disposed in the second waist region near the second end of the elongate slit opening substantially aligned with the longitudinal axis and two front elasticated regions diverging from the longitudinal axis near the first end of the elongate slit opening into the first waist region.

* * * * *

UNITED STATES PATENT AND TRADEMARK OFFICE
CERTIFICATE OF CORRECTION

PATENT NO. : 6,482,191 B1
DATED : November 19, 2002
INVENTOR(S) : Roe et al.

It is certified that error appears in the above-identified patent and that said Letters Patent is hereby corrected as shown below:

Column 5,
Line 44, please delete "sub layers" and insert therefor -- sublayers --.

Column 6,
Line 66, please delete "anise" and insert therefor -- an in use --.

Column 8,
Line 10, please delete "1000 ml" and insert therefor -- 1000 mJ --.
Line 16, please delete "50 ml" and insert therefor -- 50 mJ --.

Column 11,
Line 13, after "thereof", please insert "." (a period).
Line 26, please delete "millijoules" and insert therefor -- milliJoules --.

Column 12,
Line 54, please delete "ilinear" and insert therefor -- linear --.

Column 14,
Line 3, please delete "openings" and insert therefor -- opening --.

Signed and Sealed this

Thirteenth Day of July, 2004

JON W. DUDAS
*Acting Director of the United States Patent and Trademark Office*